(12) United States Patent
Dicorleto

(10) Patent No.: US 12,396,775 B2
(45) Date of Patent: Aug. 26, 2025

(54) SYSTEM AND METHOD FOR POSITIONING A TRACKING DEVICE

(71) Applicant: Medtronic Navigation, Inc., Lafayette, CO (US)

(72) Inventor: Matthew F. Dicorleto, Boulder, CO (US)

(73) Assignee: Medtronic Navigation, Inc., Lafayette, CO (US)

( * ) Notice: Subject to any disclaimer, the term of this patent is extended or adjusted under 35 U.S.C. 154(b) by 0 days.

(21) Appl. No.: 18/763,585

(22) Filed: Jul. 3, 2024

(65) Prior Publication Data

US 2024/0358424 A1 Oct. 31, 2024

Related U.S. Application Data

(60) Continuation of application No. 17/185,388, filed on Feb. 25, 2021, now Pat. No. 12,029,465, which is a division of application No. 15/886,439, filed on Feb. 1, 2018, now Pat. No. 10,932,840.

(51) Int. Cl.

| | |
|---|---|
| A61B 17/88 | (2006.01) |
| A61B 17/00 | (2006.01) |
| A61B 17/16 | (2006.01) |
| A61B 34/20 | (2016.01) |
| A61B 90/00 | (2016.01) |
| B25B 23/16 | (2006.01) |

(52) U.S. Cl.
CPC ...... *A61B 17/8875* (2013.01); *A61B 17/1622* (2013.01); *A61B 34/20* (2016.02); *B25B 23/16* (2013.01); *A61B 2017/00464* (2013.01); *A61B 2017/00477* (2013.01); *A61B 2017/00725* (2013.01); *A61B 17/8886* (2013.01); *A61B 2034/2051* (2016.02); *A61B 2034/2055* (2016.02); *A61B 2090/3762* (2016.02); *A61B 2090/3983* (2016.02)

(58) Field of Classification Search
CPC ........................ A61B 17/00469; A61B 34/20
See application file for complete search history.

(56) References Cited

U.S. PATENT DOCUMENTS

| | | | |
|---|---|---|---|
| 6,021,343 A | 2/2000 | Foley et al. | |
| 6,434,507 B1 | 8/2002 | Clayton et al. | |
| 7,153,308 B2 | 12/2006 | Peterson | |
| 7,166,114 B2 | 1/2007 | Moctezuma De La Barrera et al. | |
| 7,697,972 B2 | 4/2010 | Verard et al. | |
| 7,877,890 B2 | 2/2011 | Weber | |

(Continued)

FOREIGN PATENT DOCUMENTS

| | | |
|---|---|---|
| EP | 1543789 A1 | 6/2005 |
| WO | 2016141378 A1 | 9/2016 |

OTHER PUBLICATIONS

International Search Report and Written Opinion mailed May 15, 2019 in corresponding/related International Application No. PCT/US2019/016175.

(Continued)

*Primary Examiner* — Michael W Kahelin
(74) *Attorney, Agent, or Firm* — Mueting Raasch Group

(57) ABSTRACT

Disclosed is a system and method for tracking an instrument. The instrument may be tracked with one or more trackable members. The trackable members may be held relative to a handle to which the instrument is attached.

14 Claims, 4 Drawing Sheets

(56) References Cited

U.S. PATENT DOCUMENTS

| | | |
|---|---|---|
| 8,216,211 B2 | 7/2012 | Mathis et al. |
| RE44,305 E | 6/2013 | Foley et al. |
| 8,644,907 B2 | 2/2014 | Hartmann et al. |
| 8,842,893 B2 | 9/2014 | Teichman et al. |
| RE45,484 E | 4/2015 | Foley et al. |
| 9,050,108 B2 | 6/2015 | Grinberg et al. |
| 9,078,671 B2 | 7/2015 | Beale et al. |
| 9,393,039 B2 | 7/2016 | Lechner et al. |
| 9,451,999 B2 | 9/2016 | Simpson et al. |
| 9,456,827 B2 | 10/2016 | Grinberg et al. |
| 9,468,427 B2 | 10/2016 | Dicorleto et al. |
| 10,932,840 B2 | 3/2021 | DiCorleto |
| 2004/0152955 A1 | 8/2004 | McGinley et al. |
| 2004/0171930 A1 | 9/2004 | Grimm et al. |
| 2004/0199072 A1 | 10/2004 | Sprouse et al. |
| 2005/0154296 A1* | 7/2005 | Lechner .......... A61B 17/00234 600/429 |
| 2011/0313281 A1 | 12/2011 | Grinberg et al. |
| 2013/0261609 A1 | 10/2013 | Dicorleto et al. |
| 2015/0182293 A1* | 7/2015 | Yang ................. A61B 17/1703 600/424 |
| 2017/0000583 A1 | 1/2017 | Lechner et al. |

OTHER PUBLICATIONS

European Examination Report, corresponding to EP 19707926.2, Dated May 10, 2023.
1st OA for related Chinese Application No. 201980006590.X; date of dispatch: Jan. 11, 2024; 13 pages.
U.S. Appl. No. 17/185,388, filed Feb. 25, 2021, Matthew F. Dicorleto.
U.S. Appl. No. 15/886,439, filed Feb. 1, 2018, Matthew F. Dicorleto.

* cited by examiner

SYSTEM AND METHOD FOR POSITIONING A TRACKING DEVICE

CROSS-REFERENCE TO RELATED APPLICATIONS

This application is a continuation application of U.S. application Ser. No. 17/185,388 filed on Feb. 25, 2021 which is a divisional of U.S. application Ser. No. 15/886,439 filed on Feb. 1, 2018. The entire disclosures of the above applications are incorporated herein by reference.

FIELD

The present disclosure relates to a device holder, and particularly to a holder to position a trackable member.

BACKGROUND

This section provides background information related to the present disclosure which is not necessarily prior art.

In a selected procedure an instrument may be moved relative to a subject. The subject may include an external cover or shell portion and internal members or portions. The instrument may be operated to perform a procedure on the internal components while only minimally disturbing the outer shell.

In performing a procedure, therefore, an instrument may be tracked with a tracking system. The tracked position of the instrument may be displayed on a display device for viewing a determined position of the instrument. The user may view the display device to determine or understand the position of the instrument relative to the subject. It may be selected, to track more than one instrument during a selected procedure.

SUMMARY

According to various embodiments, a system for tracking an instrument is disclosed. The system includes a plurality of trackable members and a tracking member holder. The tracking member holder includes a chassis portion, an instrument guiding portion having an internal wall defining an instrument passage, a trackable member engagement portion configured to hold at least one trackable member of the plurality of trackable members relative to the chassis portion, and a handle engageable portion configured to hold the chassis portion relative to a handle.

A system for tracking an instrument is disclosed, according to various embodiments. The system includes a tracking member holder, including (i) a chassis portion, (ii) a trackable member engagement portion, and (iii) a handle engaging portion. The system may further include an instrument handle. In various embodiments, an instrument may also be configured to be held relative to the instrument handle and moved with the instrument handle.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings. Although the following is disclosed regarding an exemplary surgical procedure on a human subject, it is understood that the subject disclosure and the following claims may be directed for non-human surgical procedures and non-surgical procedure.

Figure 1:
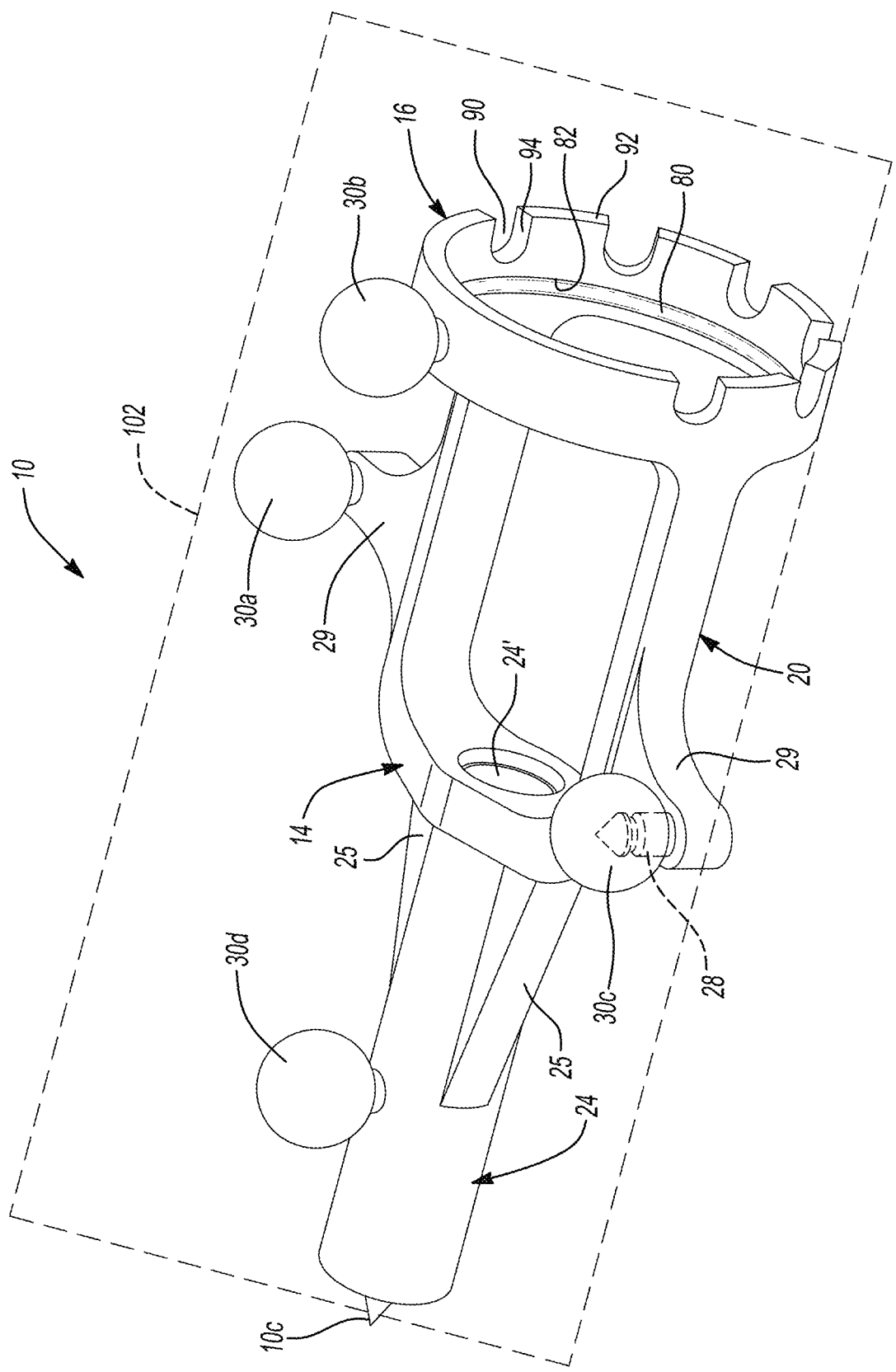
FIG. 1 is a perspective view of a tracking device holder, according to various embodiments.
Figure 2:
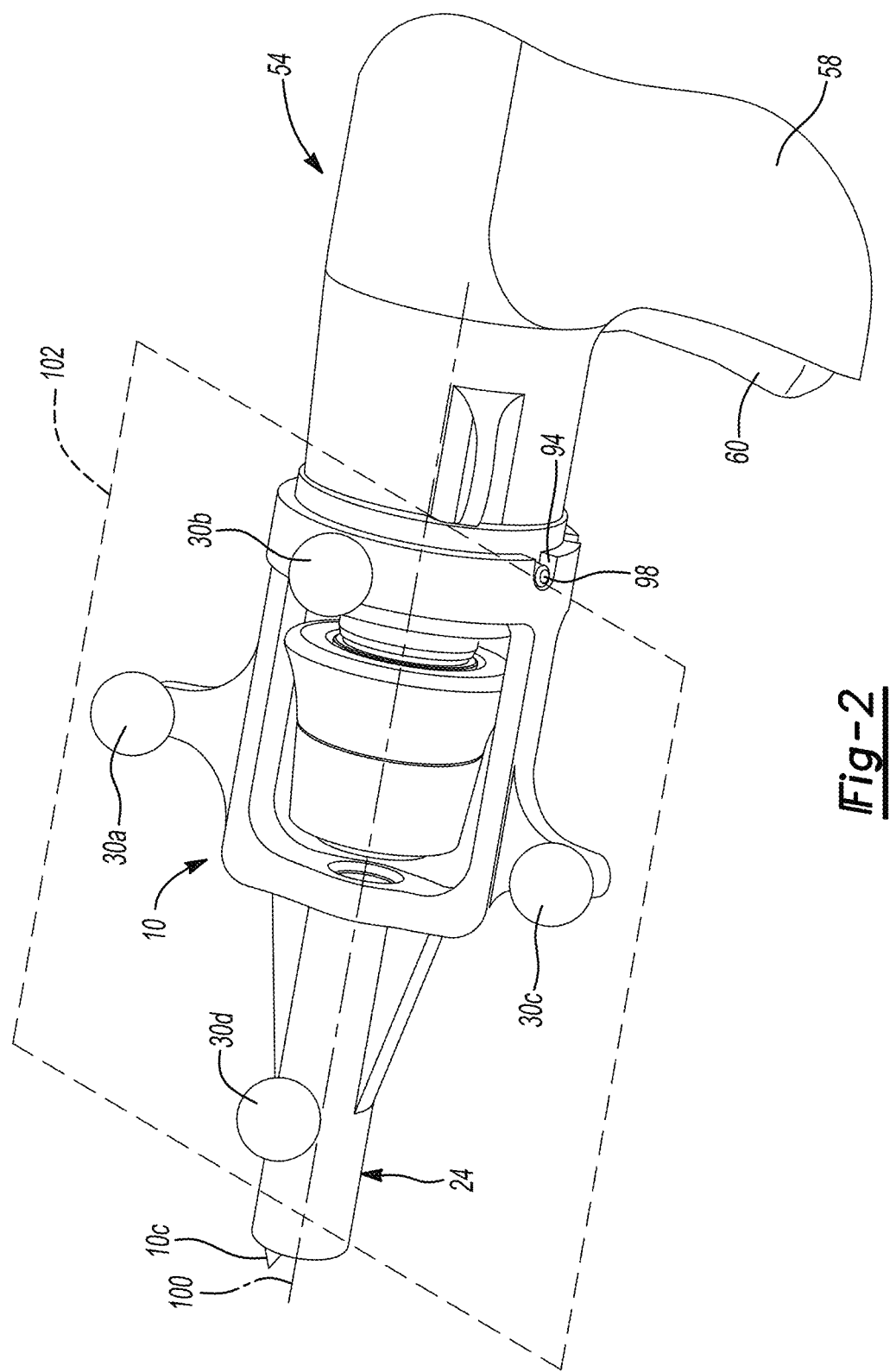
FIG. 2 is a perspective view of the tracking device holder connected to a handle, according to various embodiments.
Figure 3:
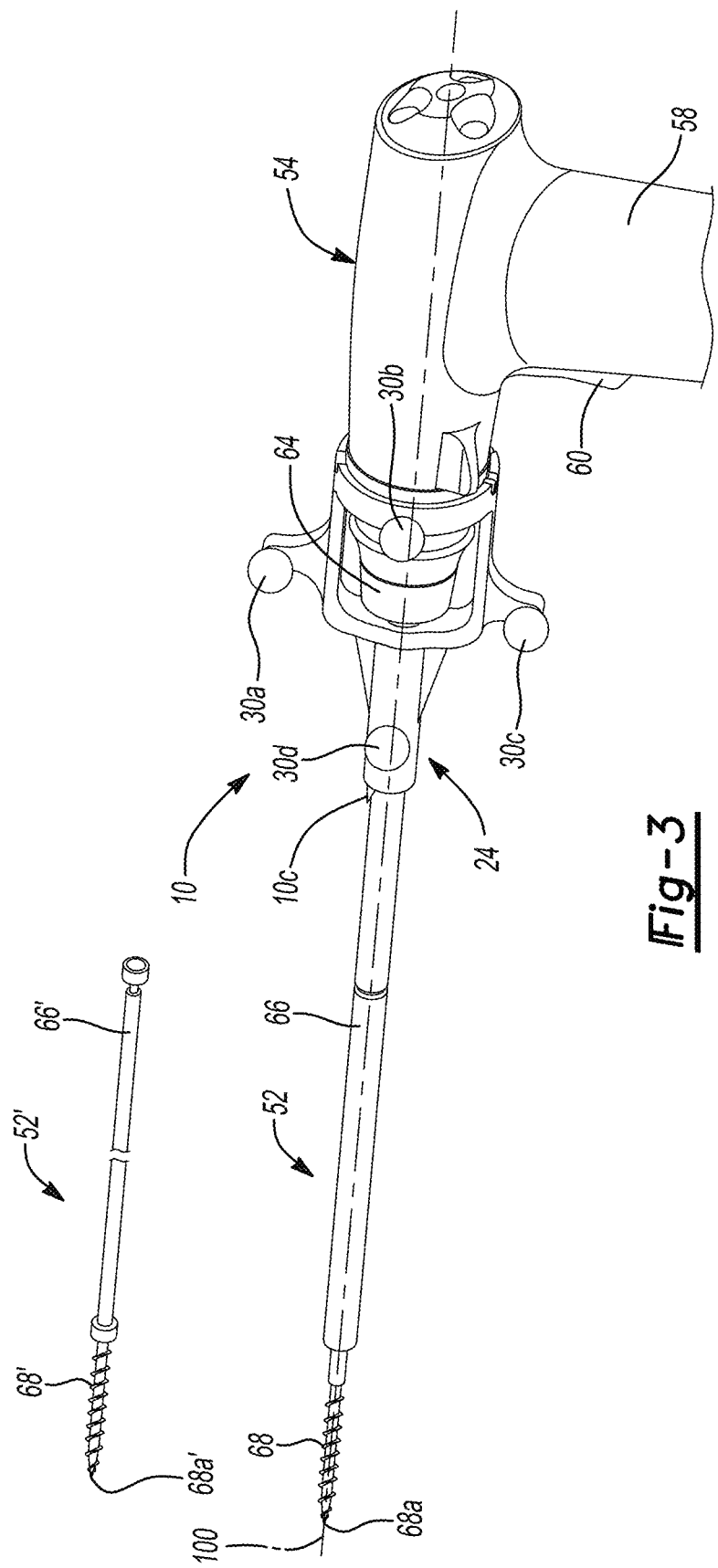
FIG. 3 is a perspective view of the tracking device holder connected to a handle and an instrument passing through the tracking device holder, according to various embodiments.

With initial reference to FIGS. 1, 2 and 3, a holder 10 is illustrated. The holder 10 may alone, or in combination with trackable members, form a tracking device that is trackable, as discussed herein. The holder 10 may also be referred to as a tracking device holding assembly, a tracking device holder, a tracking member holder, trackable member holder, or guide assembly. The holder 10 may allow the use of a driver or handle 54 with multiple instruments, as discussed herein, with only one or a single registration or calibration.

The holder 10 may include a body or chassis portion 14. The body 14 may include various features or sections. The sections may include a motor or handle assembly engaging region 16 that may be generally annular or selectively shaped to engage a driver or handle. An extension or open region or member 20 may extend from the handle assembly engaging region 16. The extension region may be generally U-shaped. A guide or passage portion 24 may extend from the extension region 20. The guide portion 24 may include a central bore of cannula 24' that may allow passage of an instrument, as discussed herein. The guide portion 24 may have buttresses 25 on one or more sides extending from the extension region 20 to assist in supporting the guide 24.

Figure 4:
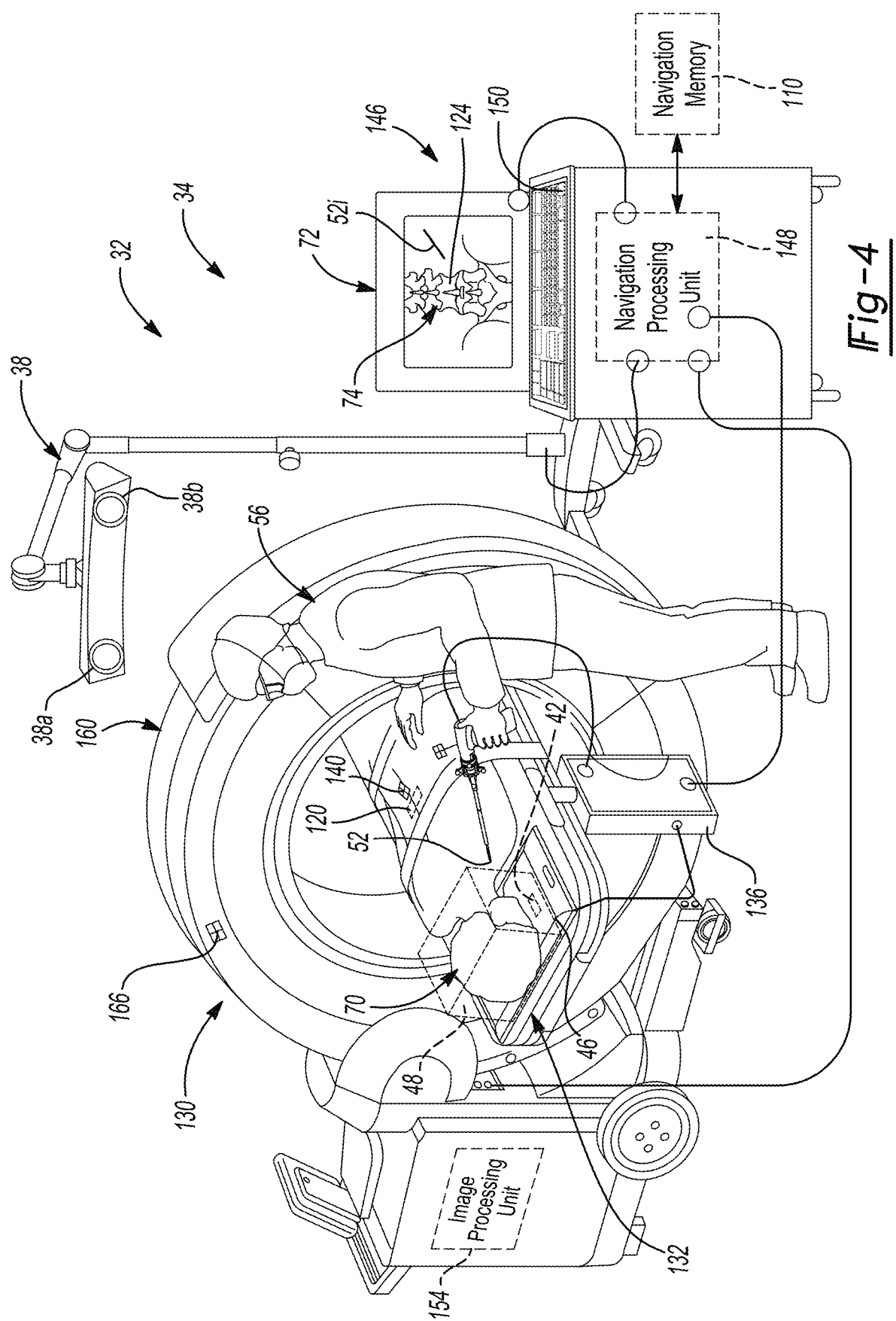
FIG. 4 is an environmental view of the tracking device holder, handle, and instrument, according to various embodiments.

The holder 10 may be formed as one piece (i.e. a single and/or unitary piece) or plurality of pieces. As discussed herein, the holder 10 may be selected to be formed of a rigid material. The rigid material may have a selected rigidity such that the holder 10 does not vary in shape or dimension during use. For example, the holder 10 maintains an initial shape during use of the holder 10 to hold tracking members 30 during use of an instrument 52 (FIG. 4).

In various embodiments, the holder 10 may be molded as a single piece of polyethylene, such as ultra-high molecular weight polyethylene, such as that used for bearing members. The material of the holder 10 may be a selected bearing material and/or a bearing material (e.g. a metal sleeve) may be provided in the bore 24'. The holder 10 may also be formed of more than one material and/or members that are fixed together. The holder 10 may be formed entirely or partially of metal, metal alloys, polymers, filled polymers (e.g. glass filled nylon), or other appropriate materials.

The material selected for the holder 10 may further include additional properties. For example, the holder 10 may have a selected anti-slip or gripping property. The holder 10 may also be selectively reusable and sterilizable (e.g. with gas sterilization, radiation sterilization, etc.). Also, or alternatively, the holder 10 may be disposable and only single use.

The holder 10 may further include one or more positions, such as posts or projections 28, for holding the tracking devices or trackable members 30. For example, the tracking member 30 may include a recess or depression that engages (e.g. frictionally engages) the projection or post 28 that extends from a wing or portion 29 of the holder 10. The wing may extend from an arm or portion of the extension portion 24. In various embodiments, the trackable members 30 may snap to the posts 28. The tracking member 30, therefore, may be removably fixed to the holder 10. The tracking member 30 may include one or more tracking members, such as a first trackable member 30a, a second track trackable member 30b, a third trackable member 30c, and a fourth trackable member 30d (referred to herein collectively of tracking or trackable members or devices 30, unless specifically referred to individually). It is understood that more or less than four of the trackable members 30 may be provided with the holder 10. Further, the trackable members 30 may be formed as one piece with the chassis 14.

With additional reference to FIG. 4, the tracking members 30 may be any appropriate tracking members that may be tracked by a tracking system 34. The tracking devices 30 may be tracked by the tracking system 34, which may be incorporated or included with a navigation system 36. In tracking the holder 10 with the tracking members 30, a position (including a three dimension location and orientation (e.g. 1 or more degree of freedom, e.g. six degrees of freedom)) of the holder 10 an item to which it is attached may be determined.

In various embodiments, the tracking devices 30 may include members that are viewable by one or more cameras of the optical or camera localizer 38. In various embodiments, therefore, the tracking system 32 may be an optical or light tracking system. In an optical tracking system the tracking members 30 may reflect (e.g. passive) or emit (e.g. active or LEDs) wavelengths of light that are visible or invisible (e.g. infrared wavelengths) that are detected by the cameras 38a, 38b. The tracking devices 30 may also or alternatively include one or more coils that may be trackable with an electromagnetic (EM) tracking system localizer. The EM localizer may include one or more coils or antennas 42 of a tracking coil array 46 that may generate a field in a navigation volume 48.

Regardless of the specific configuration or type, the tracking devices 30 may be positioned on the holder 10 to assist in tracking an instrument or tool 52, as illustrated in FIG. 3. Generally, the instrument 52 is able to rotate. For example, the driver 54 may include a motor that rotates the instrument 52 or the handle 54 is able to be used by the user 56 to rotate the instrument 52. The holder 10, however, generally holds the trackable members 30 at a selected single position relative to the handle 54 during use and for tracking.

In various embodiments, the holder 10, including the trackable members 30, may be referred to as a tracking device. The instrument 52 may be assembled or connected to a handle or drive assembly 54. The handle, as a drive assembly, 54 may include a motor for rotating the instrument 52. The motor in the handle 54 may be any appropriate motor such as pneumatic motor, an electrical motor, or the like. Generally, a user 56 may hold a selected portion of the handle 54, such as a grasping handle 58. If the handle 54 is powered, the user 56 may depress or engage one or more control mechanisms, such as a button 60, to cause the motor included within the driver 54 to move a chuck assembly 64, such as rotating the chuck assembly 64 that is generally within the extension region 20. Rotating the chuck assembly 64 may rotate the instrument 52.

In various embodiments, the instrument 52 may include an elongated shaft 66 and a working end 68. The working end 68 may be any appropriate working end such as a tap, a screw, an awl, or any appropriate working end. Further, the working end 68 may include a distal or terminal end or portion 68a. Regardless, the user 56 may engage the driver 54 to cause the working end 68 to engage a selected portion, such as a portion of a patient 70.

The instrument 52, as discussed above, can be any appropriate instrument. In various embodiments, the instrument 52 may include the working end 68 to include a tap, such as a tap to form a thread in a bore in a bone. Further, the working end 68 may include a terminal or distal end 68a. The position of the working end 68 may be selected to be precisely known and/or determined. Thus, the tap at the working end 68 may be selected to be precisely and/or knowingly positioned relative to the patient 70. For example, for forming and tapping a bore at a precise and/or preselected position for a bone screw. Further, an instrument 52' may include a screw at the working end 68'. It is understood, however, that any appropriate number of instruments may be provided with different or the same working end.

In various embodiments, the selected position of the instrument 52 may be selected to be substantially precise, such as for positioning a pedicle screw, implant, deep brain simulation probe, or the like. Accordingly, a determined position of the instrument 52 with the tracking system 32 may assist in navigation of the instrument 52 with the navigation system 34. As discussed further herein, the position of the instrument 52 may be determined with the tracking system 32 and illustrated on a display device 72, such as with an icon 52i. The icon 52i may illustrate the position of the instrument 52 relative to the patient 70 represented by an image 74. The image 74 may also be displayed on the display device 72 and the icon 52i may be superimposed thereon. The user 56 may, therefore, view the display device 72 to determine or view a representation of the instrument 52 relative to the patient 70 by viewing the icon 52i relative to the image 74.

The instrument 52, which may be a first instrument, may be substituted or changed to a different instrument, such as an instrument 52', also referred to as a second instrument 52'. The instrument 52' may include a working end 68' that may be different than the working end 68, and may include a screw which may be placed in the bore tapped with the tap 68. In various embodiments, the working end 68 may include a tap which is formed and configured to tap a portion of the patient 70, such as a vertebra, and the screw 68' may be positioned in the tapped opening or bore. During a selected procedure, the instrument 52, including the shaft 66, may be removed from the handle 54 including the chuck 64. A shaft 66' of the instrument 52' may then be positioned within the chuck 64 for driving the screw 68' into the subject or patient 70.

The holder 10 may remain fixed to the handle 54, with the connections as discussed herein, while the instrument 52 and/or 52' is positioned or repositioned (e.g. passed through the holder 10) to the handle 54. For example, in various embodiments, the shaft 66 of the instrument 52 may be first connected to the handle 54. At a selected time, such as after using the instrument 52 (e.g. to tap a bore), the shaft 66 may be withdrawn or removed through the extension or guide portion 24 of the holder 10 while the holder 10 remained attached to the handle 54. Once the instrument 52 is removed, and the shaft 66' of the instrument 52' may be passed through the guide or shaft holder 24 into the chuck 64 in a reverse manner. While the instrument 52 is removed from the tool 54 and the instrument 52' engaged therewith, the tracking device holder 10 may be maintained on the tool 54. Accordingly, the instrument 52 need be the only portion or member removed from the tool 54 and the instrument 52' positioned into the tool 54 without moving or changing the tracking device holder 10. This can reduce the time of a procedure by, for example, eliminating calibration or recalibration of the holder 10 with the trackable members relative to the handle 54 after changing an instrument relative to the handle 54.

To assist in holding or to maintain fixation of the holder 10 to the handle 54, in various embodiments, the holder 10 may include a tool or handle engagement mechanism at the tool engagement portion 16. For example, a friction engagement or holding member 80 is positioned within a receiving groove or portion 82 of the tracking device holder 10. The friction member 80 may include an O-ring formed of a selected material, such as a butyl rubber or other synthetic or natural rubber material. The ring 80 may extend or project from the groove 82 and engage an external surface or a portion of the tool 54. The engagement of the holding member 80 with the tool 54, such as the friction engagement, may not be overcome by movement of the instrument 52, 52' through the guide portion 24.

The tracking device holder 10 may be positioned at selected and fixed positions relative to the tool 54 through engagement of one or more indents 90 formed as depressions or passages in an end wall 92 and having an internal wall 94. The internal wall 94 of the indent or groove 90 may engage a holding pin 98 that extends from the tool 54. The holder 10 may then be positioned at a selected rotational position around an axis 100 extending through the tool 54. As illustrated in FIG. 1, the tracking device holder 10 may include six indents or positions 90 at the tool engaging portion 16. It is understood that more or fewer indents or positional members may be provided with the tracking device holder 10. Regardless, the holder 10 may be oriented such that when pressed on the handle 54 the pin 98 will be received within the indent 90 to rotational fix the holder 10 relative to the handle 54. It is understood, however, that the handle 54 may include one or more depressions that receives a pin or projection of the holder 10.

The tracking members 30 may be placed generally on a plane 102 or on a selected side of the plane 102. The plane 102 may be defined by at least a portion of the holder 10. Thus, the holder 10 may rotate to rotate the plane around the axis 100 and be held in the selected position relative to the handle 54. The plane 102, therefore, may be positioned in a selected, e.g. optimal view or line of sight of the localizer 38.

The engagement feature or mechanism 80 may include alternative and/or additional engagement features. For example, the tool engagement portion 16 may include an internal thread that engages an external thread defined or formed by the tool 54. The holder 10 may then be threaded onto the tool 54. Further, or alternatively thereto, a quick connect mechanism may be provided to engage the tracking device holder 10 with the tool 54. For example, a holding member or ball may be retracted into the tool 54 when engaged by the tracking device holder 10 and then rebound or be biased into the holding portion or groove 82 in the tracking device holder 10 when the tracking device holder 10 is positioned at a selected position relative to the tool 54.

Accordingly, it is understood, that the tracking device holder 10 may be held relative to the tool 54 in any appropriate manner. Further, the tracking device holder 10 may be positioned at a selected rotational position relative to the tool 54 and held at the selected position.

As discussed further herein tracking the tool 54 and/or the instrument 52, 52' may require that the tracking devices 30 be positioned at a fixed and known position relative to the tool 54 and/or the instrument 52, 52'. Accordingly, the tracking device holder 10 may hold the tracking devices 30 at a fixed and selected position relative to the tool 54 during a procedure. Prior to tracking the instrument 52, 52' (e.g. during a procedure), the tracking devices 30 may be calibrated or registered relative to a portion of the instrument 52 (e.g. the working end 68 and/or the terminal end 68a) and/or the tool 54. In various embodiments, calibration may occur with a fiducial or fixed/known point registration procedure as is generally understood in the art.

For example, calibration may occur by tracking the holder 10, including the tracking devices 30, positioned on the tool 54. With or without the instrument 52, 52' positioned within the tool 54, the positions of the tracking devices 30 relative to the tool 54 may be determined. For example, the holder 10 may engage a selected feature, such as a divot, at a known position relative to the localizer 38. The navigation system 34 may then determine the position of the tracking devices 30 relative to the tool 54. The instrument 52, 52' may then be engaged with the tool 54 and the navigation system 34 may recall from a navigation memory 110 a geometry of the instrument 52, 52'. The navigation system 34 may then, knowing the geometry of the instrument 52, 52' and the position of the tracking devices 30 relative to the tool 54, determine the position of the working end 68, 68' based upon the known geometry of the respective tools 52, 52'. It is further understood that the user 56 may enter a geometry of the instruments 52, 52' rather than having them recalled from the navigation memory 110.

Regardless, the tracking device holder 10 is used to fixedly hold the tracking devices 30 relative to the tool 54 and/or the instrument 52, 52'. Thus, the user 56 need not directly engage the holder 10. Further, the geometry of the tracking device holder 10 allows for the instrument 52 to be engaged and disengaged from the tool 54 and the instrument 52' to be engaged and disengaged from the tool 54 without removing the tracking device holder 10 or moving the tracking device holder 10 relative to the tool 54. Therefore, once the tracking device holder 10 and the tracking devices 30 positioned therewith are registered or calibrated relative to the tool 54 the instrument may be changed relative to the tool 54 without requiring recalibration of the position of the tracking devices relative to the tool and/or with the respective instruments 52, 52'.

The selected instrument 52, 52' (or other appropriate instrument), therefore, may be used to perform a procedure on the subject 70. In various embodiments, with reference to FIG. 4, therefore, the tracking device holder 10 is used by the user 56 to position and/or navigate the instrument 52 relative to the subject 70. For example, the instrument may include a tap at the working end 68 to tap (e.g. form threads in a bore) in a selected portion of the subject 70 including a vertebrae 120. The image 74 may include an image of the vertebrae 120 as a vertebrae image 124. The icon 52i may be illustrated on the display device 72 relative to the image 124.

The navigation system 34 may be used for various purposes or procedures by one or more users, such as the user 56. The navigation system 56 may be used to determine or track a position of the instrument 52 in a volume, such as the navigation or tracking volume 48. Tracking the position of the instrument 52 may assist the user 56 in determining a position of the instrument 162 even if the instrument 52 is not directly viewable by the user 56. Various procedures may block the view of the user 56, such as performing a repair or assembling an inanimate system, such as a robotic system, assembling portions of an airframe or an automobile, or the like. Various other procedures may include a surgical procedure, such as performing a spinal procedure, neurological procedure, positioning a deep brain simulation probe, or other surgical procedures on a living subject. In various embodiments, for example, the living subject may be a human subject 70 and the procedure may be performed on the human subject 70. It is understood, however, that the instrument 52 may be tracked and/or navigated relative to any subject for any appropriate procedure.

Nevertheless, in various embodiments, the surgical navigation system 34, as discussed further herein, may incorporate various portions such as those disclosed in U.S. Pat. Nos. RE44,305; 7,697,972; 8,644,907; and 8,842,893; and U.S. Pat. App. Pub. Nos. 2004/0199072, all incorporated herein by reference. Various components that may be used with or as a component of the surgical navigation system 34 may include an imaging system 130 that is operable to image the subject 70, such as an O-arm® imaging system, magnetic resonance imaging (MRI) system, computed tomography system, etc. A subject support 132 may be used to support or hold the subject 70 during imaging and/or during a procedure. The same or different supports may be used for different portions of a procedure.

Image data may be acquired during a surgical procedure or acquired prior to a surgical procedure for displaying the image 74 on the display device 72. The instrument 52 may be tracked in the trackable volume or the navigational volume 48 that is defined by the tracking system, including the localizer 38, 40. The position of the instrument 52 may be tracked in the tracking volume relative to the subject 70 and then illustrated as the icon 52i with the display device 72. In various embodiments, the icon 52i may be superimposed on the image 74 and/or adjacent to the image 74. As discussed herein, the navigation system 34 may incorporate the display device 72 and operate to render the image 74 from selected image data, display the image 74, determine the position of the instrument 52, determine the location of the icon 52i, etc.

In various embodiments, the localizer 46 may be an electro-magnetic (EM) localizer that is operable to generate electro-magnetic fields with a transmitting coil array (TCA) 42 which is incorporated into the localizer 46. The TCA 42 may include one or more coil groupings or arrays. In various embodiments, more than one group is included and each of the groupings may include three coils, also referred to as trios or triplets. The coils may be powered to generate or form an electro-magnetic field by driving current through the coils of the coil groupings. As the current is driven through the coils, the electro-magnetic fields generated will extend away from the coils 42 and form the navigation domain or volume 48, such as encompassing all or a portion of the subject 70, including spinal vertebrae 120, or other appropriate portion. The coils may be powered through a TCA controller and/or power supply 136.

The navigation domain or volume 48 may also be defined by a volume or area that is viewable by cameras of the localizer 38. In various embodiments a selected number of cameras (e.g. two cameras 38a, 38b) may view the volume 48. The volume viewable by the localizer 38 may include the navigation volume 48. The position of the tracking device or trackable members 30 may be determined relative to a patient tracker 140, that is also viewable, or relative to the localizer 38 (e.g. if the localizer 38 is fixed relative to the subject 70).

The navigation domain or volume 48 generally defines a navigation space or patient space. As is generally understood in the art, the instrument 52, such as discussed above, may include a drill, lead, etc., may be tracked in the navigation domain relative to a patient or subject 70 with the tracking assembly 10 including the trackable members 30. For example, the instrument 52 may be freely moveable, such as by the user 56, relative to the dynamic preference frame (DRF) or reference frame tracker 140 that is fixed relative to the subject 70. Both the tracking devices 10, 140 may include trackable members 30 and/or tracking or sensing coils (e.g. conductive material formed as a coil) that sense and are used to measure a magnetic field strength, etc. Due to the tracking device 10 connected or associated with the instrument 52, relative to the DRF 140, the navigation system 30 may be used to determine the position of the instrument 52 relative to the DRF 140.

The navigation volume or patient space may be registered to an image space of the patient and the icon 52i representing the instrument 52 may be illustrated at a known and tracked location with the display device, such as superimposed on the image 74. Registration of the patient space to the image space and determining a location of a tracking device, such as with the tracking device 10 relative to the DRF 140, may be performed as generally known in the art, including as disclosed in U.S. Pat. Nos. RE44,305; 7,697,972; 8,644,907; and 8,842,893; and U.S. Pat. App. Pub. Nos. 2004/0199072, all incorporated herein by reference.

The navigation system 34 may further include a navigation processor system 146. The navigation processor system 146 may include the display device 72, one or more of the localizers 38, 40, the TCA controller 136, and other portions and/or connections thereto. For example, a wire connection may be provided between the TCA controller 136 and a navigation processing unit 148. Further, the navigation processor system 146 may have one or more inputs, such as a keyboard 150, and have and/or be in communication with one or more memory systems 110, either integrated or via a communication system. The navigation processor system 146 may, according to various embodiments, include those disclosed in U.S. Pat. Nos. RE44,305; 7,697,972; 8,644,907; and 8,842,893; and U.S. Pat. App. Pub. Nos. 2004/0199072, all incorporated herein by reference, or may also include the commercially available StealthStation® or Fusion™ surgical navigation systems sold by Medtronic Navigation, Inc. having a place of business in Louisville, CO.

Tracking information, including regarding the viewed and/or triangulated position of the tracking devices 10, 140 may be delivered via a communication system, such as the TCA controller, which also may be a tracking device controller 136, to the navigation processor system 146 including the navigation processor 148. Navigation processor 148 may be a part of the work station or computer system 146 that includes the display device 72 to display the image 74. Various other memory and processing systems may also be provided with and/or in communication with the processor system 148 such as an imaging processing unit 154. The image processing unit 154 may be incorporated into the imaging system 130, such as the O-arm® imaging system, as discussed above. The imaging system 130 may, therefore, include various portions such as a source and a x-ray detector that are moveable within a gantry 160. The imaging system 130 may also be tracked with a tracking device 166.

It is understood, however, that the imaging system 130 need not be present while tracking the tracking devices, including the instrument tracking device 10. Also, the imaging system 130 may be any appropriate imaging system including a MRI, CT, etc.

Information regarding all of the tracking devices may be communicated to the navigation processor 148 for determining a position of the tracked portions relative to each other and/or for localizing the instrument 52 relative to the image 74. The imaging system 130 may be used to acquire image data to generate or produce the image 74 of the subject 70. It is understood, however, that other appropriate imaging systems may also be used. The TCA controller 136 may be used to operate and power the TCA 46 and or the localizer 38, as discussed above.

In various embodiments, therefore, and with continuing reference to FIGS. 1-4, the holder 10, also referred to as the tracking device or assembly, may be tracked with the tracking system 32, such as with the localizer 38, to determine a position of the instrument 52 with the navigation system 34. As discussed above, tracking may occur due to the tracking members 30 that are held by the holder 10 relative to the handle 54. During a procedure, however, the instrument 52 and/or 52' may be removed and replaced with the other of the instrument 52, 52' without removing the holder 10. Thus, only the instrument 52, 52'; may be removed from the handle 54. It is understood, however, that other additional instruments may also be positioned relative to the handle 54 after removing the exemplary disclosed instruments.

As discussed above, the holder 10 including the trackable members 30 may be a registered and/or calibrated relative to the handle 54 prior to tracking any instruments and/or performing a procedure on the subject 70. In various embodiments, therefore, the holder 10 may be fitted to the handle 54, as discussed above, and then calibrated or registered. The calibration may include predetermining (e.g. during a manufacture) a geometry of the holder 10 and/or the members 30 relative to the handle 54 and saving the predetermined geometry. The predetermined geometry may then be recalled, such as by the user 56, once assembling the holder 10 to the handle 54. The navigation processing unit 148 may recall from the navigation memory 110 the predetermined geometry and use the recalled predetermined geometry for calibration of the holder 10 relative to the handle 54. The geometry of the instrument, such as the instrument 52, can also then be calibrated and/or recalled from the navigation memory 110 to be able to track the position of the instrument 52, including the working end 68.

Alternatively, or in addition to a lookup table or recalling from memory, the tracking system 32 may be calibrated during use. For example, the holder 10 may be positioned or fit to the handle 54 in a selected manner, as discussed above. A portion of the holder 10, once fitted to the handle 54, may then be touched to a known or registerable portion, such as a divot formed by the DRF 140. For example, a distal end of the holder or selected portion thereof, such as a projection 10c may engage a divot (e.g. shaped indent in the DRF 140). Once the distal end, for example the projection 10c, engages the divot of the DRF 140 the tracking system 32 may be operated to calibrate or determine a position of the projection 10c in the navigation volume 70. Therefore during a procedure the geometry or position of at least a portion of the holder 10 may be determined during a procedure. Then the instrument 52 fixed to the handle 54 may also be touched to the divot of the DRF 140 to know the distal end of the working end 68 relative to the end or projection 10c of the holder 10.

Upon removal of the instrument 52 and insertion of the instrument 52', the calibration of the holder 10 relative to the handle 54 need not be repeated, especially if and/or only if the holder 10 is not removed from the handle 54 during removal of the instrument 52 and/or insertion of the instrument 52'. The instrument 52 may be removed through the holder 10 and the instrument 52' may be inserted into the handle 54 through the holder 10.

Accordingly, the holder 10, including the trackable members 30, may be calibrated relative to the handle 54 at a single time and only one time, such as prior to a procedure or during a procedure. After the calibration, instruments may be removed and inserted, such as serially or sequentially, with the handle 54 without requiring recalibration of the holder 10 including the trackable members 30. Thus, the user 56 may select different instruments and attach the different instruments at selected different times to the handle 54 without requiring recalibration of the holder and the trackable members 30 to continue tracking and navigation of the selected instrument 52. Therefore the position (i.e. including a three dimensional location and selected degrees of freedom of orientation (three degrees of freedom)) may be made with the tracking system 32 to allow for navigation of the instrument 52 with the navigation system 34.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method of tracking a first instrument and a second instrument with a trackable member, the method comprising:

forming a trackable member engagement portion of a tracking member holder that extends along a longitudinal axis from a proximal end to a distal end, the trackable member engagement portion configured to hold at least one trackable member of a plurality of trackable members;

forming an instrument guiding portion at the distal end of the tracking member holder having an internal wall defining an instrument passage extending along the longitudinal axis to allow passage of the first instrument and the second instrument to connect to a handle;

forming a handle engageable portion at the proximal end of the tracking member holder configured to removably hold the tracking member holder relative to the handle; and forming an extension axially extending along the longitudinal axis and positioned between the instrument guiding portion and the handle engageable portion;

wherein the handle engageable portion is spaced apart from the instrument guiding portion with the extension.

2. The method of claim 1, further comprising:

fixing a plurality of trackable members to the trackable member engagement portion.

3. The method of claim 2, further comprising:

connecting the tracking member holder to the handle; and
calibrating the tracking member holder relative to the handle.

4. The method of claim 3, further comprising:

connecting the first instrument to the handle through the instrument guiding portion; and
operating a tracking system to track at least one trackable member of the plurality of trackable members.

5. The method of claim 4, further comprising:

removing the first instrument from connection with the handle while maintaining the connection of the tracking member holder to the handle;
connecting the second instrument to the handle through the instrument guiding portion of the tracking member holder while connected to the handle.

6. The method of claim 5, further comprising:

operating the tracking system to track at least one trackable member of the plurality of trackable members without calibrating the tracking member holder relative to the handle.

7. The method of claim 1, wherein forming includes molding the tracking member holder from a polymer material.

8. The method of claim 4, wherein connecting the first instrument to the handle includes passing the first instrument through the instrument guiding portion to couple to the handle spaced apart from the instrument guiding portion; and rotating the first instrument within the instrument guiding portion using the handle.

9. The method of claim 1, wherein forming the trackable member engagement portion includes forming a first trackable member engagement portion on the handle engageable portion, forming a second trackable member engagement portion on the instrument guiding portion, and forming a third trackable member engagement portion on the extension, wherein the first, second and third trackable member engagement portions is each configured to carry a trackable member.

10. The method of claim 1, wherein forming the handle engageable portion includes forming an annular shaped handle engageable portion that is annularly positioned about the longitudinal axis of the tracking member holder and configured to be removably attached to the handle.

11. The method of claim 10, further comprising forming a plurality of notches into the annular handle engageable portion, wherein each notch of the plurality of notches is configured to engage a protrusion of the handle to rotatably retain the tracking member holder relative to the handle.

12. The method of claim 1, wherein forming the extension further includes forming a u-shaped extension that axially extends between the handle engagement portion and the instrument guide portion.

13. The method of claim 1, wherein forming the instrument guiding portion further includes forming a pair of opposed buttresses extending from the instrument guiding portion and configured to provide support for the instrument guiding portion.

14. The method of claim 1, wherein forming the extension further includes forming a u-shaped extension having a pair of opposed wing members extending from the formed u-shaped extension, each wing member having a trackable member engagement portion configured to hold at least one trackable member.

* * * * *